United States Patent [19]

Scharff et al.

[11] Patent Number: 4,476,017
[45] Date of Patent: Oct. 9, 1984

[54] REMOVABLE SYNTHESIS COLUMN

[75] Inventors: Daniel H. Scharff, Mountain View; Lev J. Leytes, Palo Alto, both of Calif.

[73] Assignee: Beckman Instruments, Inc., Fullerton, Calif.

[21] Appl. No.: 500,661

[22] Filed: Jun. 3, 1983

[51] Int. Cl.³ ............................................. B01D 15/08
[52] U.S. Cl. ................................. 210/94; 210/198.2; 422/70
[58] Field of Search .................... 210/656, 659, 198.2, 210/94; 55/67, 197, 386; 422/70

[56] References Cited

U.S. PATENT DOCUMENTS

| 2,545,789 | 3/1951 | Miller | 210/164 |
|---|---|---|---|
| 3,240,342 | 3/1966 | Callahan, Jr. et al. | 210/232 |
| 3,250,395 | 5/1966 | Blume | 210/198.2 |
| 3,440,864 | 4/1969 | Blume | 210/656 |
| 3,463,320 | 8/1969 | Patterson | 210/94 |
| 3,492,396 | 1/1970 | Dalton et al. | 210/94 X |
| 3,529,726 | 9/1970 | Keenan | 210/266 X |
| 4,180,383 | 10/1979 | Johnson | 422/69 |
| 4,181,853 | 1/1980 | Abu-Shumars | 250/304 |
| 4,242,207 | 12/1980 | Ford | 210/500.1 |
| 4,280,905 | 7/1981 | Gunkel et al. | 210/198.2 |
| 4,294,699 | 10/1981 | Herrmann | 210/287 |
| 4,350,595 | 9/1982 | Gunkel | 210/656 |

OTHER PUBLICATIONS

Rainin Inst. Co. Catalog C3-82, pp. 27, 34, and 78, 1982.

Primary Examiner—John Adee
Attorney, Agent, or Firm—R. J. Steinmeyer; F. L. Mehlhoff; T. R. Schulte

[57] ABSTRACT

A column for use in DNA synthesis. The column is transparent and is disposable to allow access to the resin beads within the column. The column includes end caps which are engageable with a housing and a screw to secure the column in the housing.

9 Claims, 4 Drawing Figures

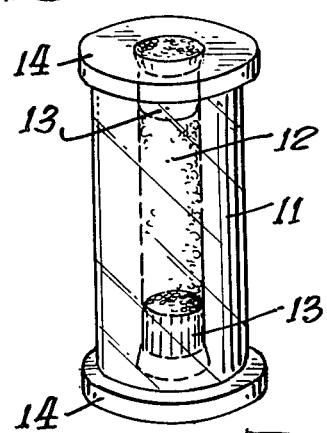
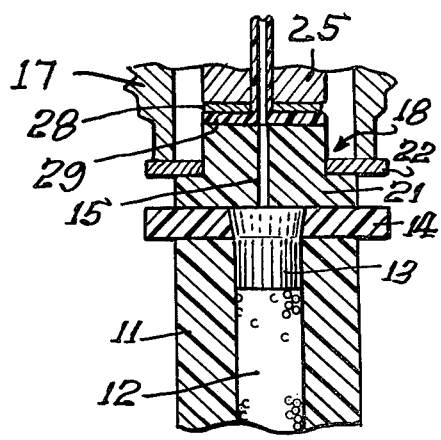
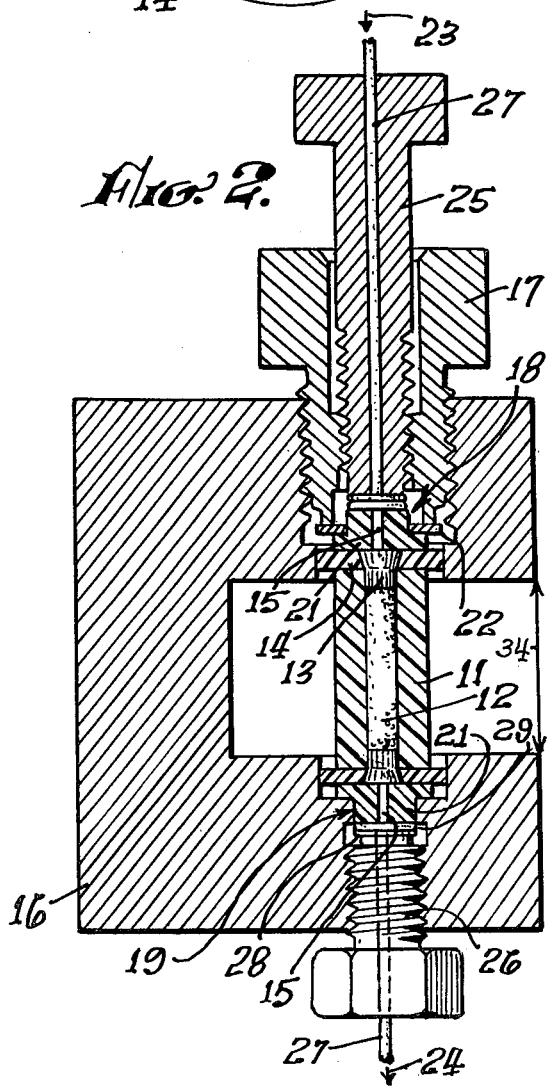
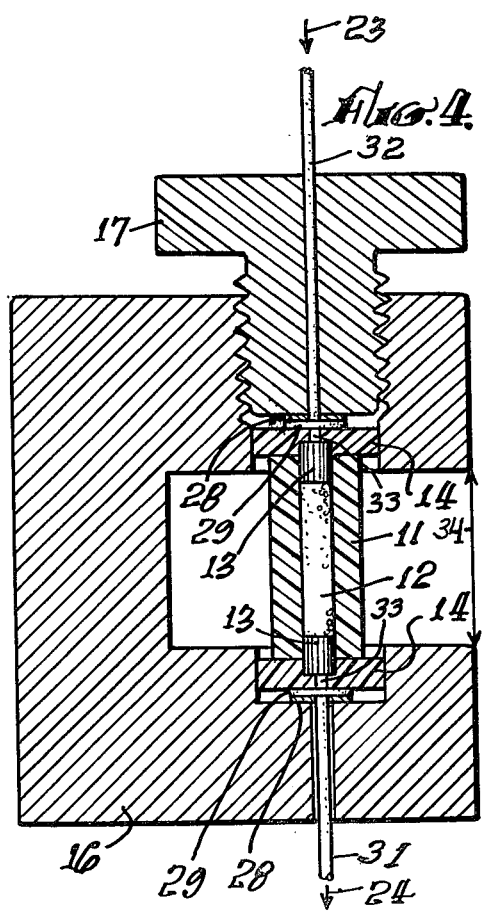

REMOVABLE SYNTHESIS COLUMN

BACKGROUND OF THE INVENTION

1. Field of the Invention

This invention relates to the field of biochemical instrumentation. More particularly, the invention relates to DNA synthesis. By way of further characterization, but not by way of limitation thereto, the invention is a disposable DNA synthesis column which includes a transparent tube for viewing of the resin beads within the tube. The column is secured into and removed from a housing by means of a screw threadably engaged with the housing.

2. Description of the Related Art

Separations performed by liquid chromatography have employed separation columns for a number of years. In general, these columns are expensive to purchase and time consuming to install and remove. The separation material in those columns is re-used and the columns may be utilized for a year or more without being replaced. The separation material in the column is washed after each use by eluting a wash solution through the column. DNA synthesis, on the other hand, requires that the resin beads in the column be removed after the synthesis in order to obtain the synthesized DNA present on the resin beads. Because the column must be removed after each separation, the difficulty in removing and installing columns is a very important consideration in DNA synthesis. In addition, while the columns must be removable, they also must be tightly sealed to prevent contamination and to prevent leakage of the eluent from a column.

In the past, the removable and disposable portions of the DNA synthesis columns were complicated to separate. That is, a number of O-rings, collars and threadable assemblies with nuts and fittings were employed which made the column expensive and complicated and thus difficult to take apart. The portion of the column which was replaced was the tube portion with the packing material or resin beads. The rest of the fittings were re-used. Many of these columns, because of the difficulty in fitting a large number of parts together, incorporate a dead volume area within the column. That is, there are unintended spaces in the column into which the liquid would be trapped. Because of the dead volume, errors in the synthesis could occur if a portion of a first liquid chemical remained in the dead volume while the next liquid in the series was flowing through. That is, if the first liquid filled the dead volume and then gradually was replaced during elution of the second liquid, then this first liquid would be mixed with the second liquid and could result in the wrong sequence on the DNA chain.

Previously employed columns have been made of opaque material. That is, because of the seals required and because of the amount of handling which must be done to the column during replacement of the tube, the columns had to be made of a relatively durable material. In those situations where the tube was made of a transparent material such as glass or plastic, the tube was relatively difficult to fabricate since flanges and the like were required to seat against O-rings or the like to provide a liquid seal. Thus, metal tubes were preferred. It is desirable in DNA synthesis to view the synthesis itself and thus, columns employing a transparent tube would be desirable.

SUMMARY OF THE INVENTION

The invention is a DNA synthesis column which employs a transparent tube. The resin beads are contained in the tube and a filter means is included at each end of the tube. A sealing means at each end of the tube includes a port alignable with the opening in the tube. The sealed unit is placed in a housing which includes a supply line in alignment with the port through the sealing means. The unit is secured by a threaded screw which holds the unit tightly in the housing. The tube is viewable through an opening in the housing. Because the tube is transparent, the synthesis is viewable to an operator.

BRIEF DESCRIPTION OF THE DRAWINGS

FIG. 1 is a perspective view of the column;

FIG. 2 is a sectional view of the column secured in the housing;

FIG. 3 is a fractional side sectional view of the upper portion of the column and the related fittings shown in FIG. 2; and FIG. 4 is a sectional view of an alternate embodiment of the column secured in the housing.

DESCRIPTION OF THE PREFERRED EMBODIMENT

Referring to FIG. 1, a tube 11 contains resin beads 12. A filtering means which may include frits 13 holds a sealing means which may include end caps 14 in each end of tube 11. Frits 13 are porous and in alignment with the opening through tube 11 such that a liquid may flow through the entire unit.

Referring to FIG. 2, tube 11, frits 13 and resin beads 12 are held in housing 16 by the cooperation of end caps 14 and a securing means which may include a screw 17 and upper adapter 18 and lower adaptor 19. Adaptors 18 and 19 include ports 15 to allow liquid to pass therethrough. Adaptor 18 includes inert disc 21 and metal washer 22 while adaptor 19 includes only inert disc 21. Ports 15 are alignable with a supply line 23 and an effluent line 24 in upper line connector fitting 25 and lower line connector fitting 26, respectively. Metal washer 22 prevents deformation or twisting of inert disc 21 which might otherwise cause a leak. Upper line connector fitting 25 threadably engages with screw 17 and lower line connector fitting 26 threadably engages with housing 16. Line connector fittings 25 and 26 include a conduit 27 which is flanged at 29 and backed up by backup washer 28. These line connector fittings are commercially available from Altex Scientific, Inc., Berkeley, Calif. Resin beads 12 are viewable through glass tube 11 and through opening 34 in housing 16.

Referring to FIG. 3, frits 13 and end caps 14 are chamfered as shown such that frits 13 hold end caps 14 on tube 11. The interrelationships between end caps 14, upper adaptor 18 and upper line connector fitting 25 are more clearly shown. Screw 17 contacts washer 22 on adaptor 18 to pressure inert disc 21 against end cap 14 and end cap 14 against tube 11. Thus, a liquid seal is effected.

Referring to FIG. 4, tube 11, frits 13 and resin beads 12 are held in a housing 16 by the cooperation of end caps 14 and screw 17. In this embodiment, adaptors 18 and 19 are removed and end caps 14 seal directly to flanges 29 on conduits 31 and 32 when screw 17 is tightened. Lower conduit 31 becomes part of housing 16 and upper conduit 32 becomes part of screw 17. Frits 13 are secured to end caps 14 by conventional means and are recessed into end caps 14 as shown. Ports 33 allow liquid to flow through end caps 14.

MODE OF OPERATION

Referring to FIG. 1, end caps 14, frits 13 and resin beads 12 are manufactured with tube 11 such that a leak-proof seal between end caps 14 and tube 11 can be achieved when the column is installed in housing 16. The operator takes the column and places it into housing 16 with adaptors 18 and 19 are either end such that ports 15 are aligned with conduits 27. Screw 17 is then engaged with housing 16 so as to secure end caps 14 in housing 16. Conduits 27 in line connector fittings 25 and 26 are aligned with ports 15 adaptors 18 and 19 such that when the unit is assembled a liquid may flow through supply line 23, port 15, frit 13, resin beads 12, second frit 13, port 15 and effluent line 24. Metal washer 22 is part of upper adaptor 18 as shown more clearly in FIG. 3. This prevents screw 17 from seating against inert disc 21 such that the surfaces of disc 21 are not damaged. That is, when screw 17 is tightened, washer 22 protects disc 21 in order that the sealing surfaces between adaptor 18 and end cap 14 are not deformed or scratched by rotation of adaptor 18. Lower adaptor 19 does not include a metal washer because there is no screw or other attaching device to damage the seal between disc 21 and end cap 14.

Glass tube 11 is fabricated to provide a leak-proof connection to end caps 14. Tube 11 has a controlled internal diameter. Frits 13 are made out of an inert material such as porous polyethylene. Frits 13 are frictionally held in tube 11 and hold end caps against tube 11 by means of the chamfer as shown in FIG. 3. End caps 14 center tube 11 in housing 16 seal against tube 11 and adaptors 18 and 19 when secured in housing 16. After the synthesis has been performed, screw 17 is unscrewed and the column assembly is removed from the housing. The column may be disassembled by removing the end caps and frits to allow access to resin beads 12 which contain the synthesized DNA or other materials. The column assembly may then be disposed of a new one inserted for the next synthesis. Alternatively, the column assembly could be washed, packed and re-used.

There is an opening 34 in housing 16 which allows an observer to view tube 11 and thus resin beads 12 during the synthesis. Thus, the actual synthesis as the liquid flows through tube 11 and resin beads 12 may be observed. There is no dead volume in the column because end caps 14 are soft enough to seal directly to tube 11. End caps 14 are preferably made of Teflon.

The column is a low cost item as opposed to prior columns which are relatively expensive. In addition, because the column is easy to install or remove, substantial time is saved. Because of its low cost, the column may be disposable. The column may be disassembled after the synthesis and the beads extracted from the tube. The tube, end caps and frits may then be disposed of. Because a new column may be used each time, new sealing surfaces will be employed, thus increasing the reliability of the device. The fact that there is no dead volume in the column prevents possible complications due to liquid remaining in the dead volume. The transparent tube allows observation of the separation through the housing. In addition, column size may be varied such that tubes with different internal diameters may be employed as long as the end caps remain the same size to fit in the housing. Alternatively, the housing itself could be varied such that different size columns could be employed while maintaining the same size for the external configurations of the housing to fit into the instrument. Because the housing is rigid, there is a leak-proof connection between the glass column and the supply and eluent lines. Because the supply lines, adaptors, end caps, tube, and frits are made of inert materials such as plastic or glass,, the organic chemicals used in the synthesis do not contact reactive materials such as metal which has been employed in prior columns.

While the invention has been disclosed with respect to a preferred embodiment thereof, it is not to be so limited that changes and modifications may be made which are within the full intended scope of the invention as defined by the appended claims. For example, if a precision outside diameter tubing was used, then the end caps could be configured in a cup shape which fit tightly over the outside diameter of the tubing. The column could also be made from a heavy walled plastic tubing rather than glass. This possibly would be a cost savings but would eliminate the transparent nature of tube 11. The resin beads could be formed into a pellet either by fusing them together or adding a polymer resin. This would allow the frits to be part of the machine rather than part of the column.

The device disclosed herein could also be used in liquid chromatography, peptide synthesis or in any other application where chemically active liquid has to be flowed through a substance attached to a solid support or enclosed in a package.

What is claimed is:

1. A synthesis column assembly for use in a DNA synthesis instrument, comprising:
    (a) a tube defining a passage extending the length of said tube, said tube terminating in a first end and a second end;
    (b) first and second filtering means for filtering a liquid flowing through said tube, each filtering means having one end extending into and being frictionally held by a respective end of the passage;
    (c) first and second sealing means for sealing the ends of the tube to the DNA synthesis instrument, each sealing means defining an opening for receiving the other end of a respective filtering means;
    (d) whereby each sealing means is held against the respective end of the tube by the respective filtering means.

2. The assembly of claim 1 in which the passage contains resin beads that are held in place by the filtering means.

3. The assembly of claim 1 in which the depths of the openings of the sealing means are less than the thicknesses of the sealing means, and in which the sealing means define liquid flow passages that have sizes similar to those of the connecting lines through which the instrument supplies liquid to the column assembly.

4. The assembly of claim 1 in which the openings of the sealing means extend entirely through the sealing means.

5. The assembly of claim 4 in which said other ends of the filtering means and the openings of the respective sealing means have matching tapers.

6. The assembly of claim 4 in which the outer ends of the filtering means are flush with the outer surfaces of the respective sealing means.

7. The assembly of claim 1 in which the tube is transparent.

8. The assembly of claim 1 in which the tube is a glass tube.

9. The assembly of claim 1 in which the tube is a transparent plastic tube.

* * * * *